United States Patent [19]

Hetrick

[11] Patent Number: 4,615,772

[45] Date of Patent: Oct. 7, 1986

[54] ELECTROCHEMICAL GAS SENSOR

[75] Inventor: Robert E. Hetrick, Dearborn Heights, Mich.

[73] Assignee: Ford Motor Company, Dearborn, Mich.

[21] Appl. No.: 744,071

[22] Filed: Jun. 12, 1985

[51] Int. Cl.⁴ ............... G01N 27/26; G01N 27/46; G01N 27/58
[52] U.S. Cl. ............................ 204/1 T; 204/400; 204/431
[58] Field of Search ............ 204/1 T, 1 Y, 400, 424, 204/426, 431

[56] References Cited

U.S. PATENT DOCUMENTS 4,544,470 10/1985 Hetrick .............................. 204/248

OTHER PUBLICATIONS

"Photoelectrochemistry" by Allen J. Bard, *Science*, vol. 207, No. 4427, Jan. 1980, pp. 139–144.
"Visible Light Induced Cleavage of Water Into Hydrogen and Oxygen in Colloidal and Microheterogeneous Systems" by John Kiwi et al., *Structure and Bonding 49*, (1982) pp. 37–39 and pp. 101–125.
"Photoelectrochemistry and Heterogeneous Photocatalysis at Semiconductors" by Allen J. Bard, *Journal of Photochemistry*, 10, (1979) pp. 59–75.

*Primary Examiner*—Aaron Weisstuch
*Attorney, Agent, or Firm*—Peter Abolins; Robert D. Sanborn

[57] ABSTRACT

A planar photoelectrochemical sensing structure includes a thin, porous layer of photoactive semiconductor powder material deposited on an electronically conducting catalyst film which has been fabricated in two regions separated by a narrow stripe. Using incident light absorbed by the semiconductor, the structure is suited to photosensitizing redox reactions of chemical species introduced to the structure in an aqueous gas-phase environment. If photocarriers generated by the incident light are prevented from reaching one of the catalyst regions, for example by use of a light shield, then an EMF develops between the two catalyst regions. The magnitude of the EMF varies with the concentration of one of the gaseous reactants and thus provides a measure of the concentration.

16 Claims, 10 Drawing Figures

ELECTROCHEMICAL GAS SENSOR

BACKGROUND OF THE INVENTION

1. Field of the Invention

This invention relates to structures employing semiconductor powders and thin catalyst films which can photosensitize chemical reduction-oxidation (redox) reactions and simultaneously provide an electrical output which is a measure of one of the chemical species involved in the reaction.

2. Prior Art

FIG. 1 shows a schematic diagram of a prior art, conventional photoelectrochemical (PEC) cell 10 in which a semiconductor 11 of macroscopic dimensions is connected by an external circuit 12 to a counter electrode 13. Both semiconductor 11 and counter electrode 13 are immersed in an electrolyte solution 14, advantageously aqueous, which contains chemical species (redox species identified as D− and A+) which are subject to either oxidation or reduction reactions that occur with the transfer of electronic charge at the surfaces of semiconductor 11 and counter electrode 13.

Light of energy greather than the energy of the semiconductor electron bandgap is made to illuminate the semiconductor. As a result, pairs of free electrons 15 and holes 16 are generated near the illuminated surface. Under appropriate conditions for the energy level position of the redox levels in the electrolyte relative to the conduction and valence band energy positions in the semiconductor, the electrons and holes can transfer to the redox species thereby effecting the redox reactions. The various processes and conditions involved are discussed by H. Gerischer in *Physical Chemistry—An Advanced Treatise*, H. Eyring, D. Henderson, W. Jost. Eds. (Academic Press, New York, 1970), pp. 463–542.

FIG. 1 illustrates a typical situation for an n-type semiconductor where surface electric fields caused by the equilibration between electrolyte redox levels and the semiconductor Fermi level draws photoinduced holes to the semiconductor surface to oxidize redox species D− to D while electrons pass through the external circuit to reduce A+ to A at the counter electrode. At steady state, the electronic current $I_e$ in the external circuit is matched by an equal and opposite ionic current $I_i$ in the electrolyte. In summary, the semiconductor acts as a photosensitizer for carrying out the reaction $D-+A+\rightarrow D+A$. For example, $TiO_2$ sensitized photodecomposition of formic acid and other carboxylic acids in aqueous environments is well known.

Such PEC cells have a number of applications. Using the example of FIG. 1, if the reduced species is at a higher energy than the oxidized species, there is a net storage of incident radiant energy as chemical energy, as in a photoelectrosynthetic cell. The PEC splitting of $H_2O$ is an example. If the recuced species is at a lower energy than the oxidized one, no energy has been stored. Rather the PEC system has catalyzed a thermodynamically downhill reaction. An example is the photocatalytic decomposition of acetic acid to methane and carbon dioxide.

In a regenerative cell, the species oxidized at the semiconductor is also reduced at the counter electrode so that there is no net change in the energy stored in the electrolyte. An example of this type of reaction occurs if $O_2$ is dissolved in the electrolyte in which case $O_2$ would be reduced to $H_2O$ or $OH^-$ at the cathode while $H_2O$ or $OH^-$ would be oxidized to $O_2$ at the anode. However, the current in the external circuit can be used to drive an electrical load, as in a photovoltaic cell. These and other device possibilities have been described by Bard (A. J. Bard, *Science* 207, 139 (1980)).

One advantage of the PEC cell over the solid state photovoltaic cell is that it is produced quickly by simply immersing the semiconductor in the electrolyte. Secondly, light is absorbed in the region of the surface electric field of the semiconductor which causes the electron and hole to separate before they recombine. In solid state cells, the high electric field separation region is frequently at a greather distance from the surface of the semiconductor. This necessitates higher quality and higher cost material so as to allow the carriers to diffuse to this region before they recombine.

A microscopic version of a prior art PEC cell is shown schematically in FIG. 2. Here microscopic semiconductor powder grains 20 are dispersed in an electrolyte solution 21 again containing redox species D− and A+. Typically, these powder grains are submicron in dimension. The external circuit and counter electrode of FIG. 1 are replaced by a piece of catalytic material 22, typically a metal such as platinum, attached to a region of the semiconductor. The attachment can be accomplished by photochemical means. When the powder dispersion is illuminated, processes occur similar to those described for the macroscopic system of FIG. 1. Holes are drawn to the semiconductor surface where they oxidize D− while electrons move to the catalyst region where they reduce A+. The electronic flow in the grain amounts to an electronic current $I_e$ while the current loop is completed in the electrolyte by ionic current $I_i$. Thus, the grains act as microscopic short-circuited PEC cells. The powder has the advantage of providing much more reactive surface area. A disadvantage is not having an external circuit essential for photovoltaic and other electrical device applications. Writings by Gratzel et al (J. Kiwi, K. Kalyanasundaram, and M. Gratzel, *Structure and Bonding* 49, Springer-Verlag, Berlin, p. 37, (1982)) and Bard (A. J. Bard, *J. of Photochem.* 10, 59 (1979)) discuss many of the details of the microscopic system and the numerous modifications that can be attempted to make the system more effective under different circumstances.

In principle, typical electrochemical (EC) cells including PEC cells can be adapted for use as a sensor of one of the chemical species involved in the cell reaction. One way to do this involves a modification to the cell structure so that the species to be sensed could be isolated in the vicinity of the electrode where it is taken up into the electrolyte in one of the EC reaction steps. For example, $O_2$ can be sensed with an arrangement where it is spatially isolated next to a cathodically polarized electrode in a cell with an appropriate electrolyte. The amount of current passing through the cell depends on the oxygen concentration near the electrode and provides a measure of the oxygen concentration. Such a cell has been described by L. C. Clark Jr., R. Wold, D. Granger, and F. Taylor, *J. Appl. Physiol.* 6, 189 (1953). A similar arrangement could be made with the PEC cell shown in FIG. 1. In this case, the $O_2$ would have to be isolated in a region near counter electrode 13. For the appropriate illumination intensity, counter electrode 13 would become cathodically polarized and the amount of current drawn in the external circuit would provide a measure of the oxygen concentration. Numerous chemical species could be sensed by this means. Using the macroscopic structure of FIG. 1, the PEC method has no major advantage over the EC method except where an optical source of power would be advantageous. The use of the microscopic PEC system for such a sensor is obviated by the absence of an ability to make a significant electrical contact with the dispersed semiconductor powder. The present invention describes a new structure and method for making a PEC gas sensor. The structure is especially suited to gas phase sensing and the PEC method in this case provides advantages over other EC methods.

SUMMARY OF THE INVENTION

The present invention includes an EC photocatalytic structure for the photogeneration of complimentary oxidation and reduction products when exposed to light of appropriate wavelengths in the presence of suitable reactants. For example, the reactant can be water, with oxygen and hydrogen being the oxidation and reduction products, respectively. The structure includes a porous layer (typically several microns in thickness) of semiconducting powder which is positioned above a thin film of material which catalyzes either the oxidation or reduction half reactions that occur simultaneously within the structure. The porous layer may be dosed with an electrolyte (appropriate for the desired photochemistry) to increase the ionic conductivity within the pore volume of the layer. The thin film of catalyst material is also an electronic conductor which can be deposited (in the absence of the powder overlayer) onto a substrate in a number of spatially separated regions. Because of the electronic conductivity, external circuitry can be attached to the different regions of the catalyst material to measure the electrical properties of the powder overlayer.

The structure is advantageous for photosensitizing reactions in which the reactant is introduced to the porous layer from an ambient gas phase. Light incident on the outer surface of the powder layer creates electron hole pairs in this outer region. These carriers separate within the porous layer, with the photogenerated minority carriers remaining near the outer surface while the excess majority carriers accumulate at the interior surface. Under appropriate energy conditions, the separated carriers take part in redox reactions. The electrical loop between the substrate and the outer surface of the porous layer of semiconductor powder can be closed by ionic conduction through the electrolyte in the pore volume.

Electronic carriers cannot reach an underlying thin-film catalyst of a spatially separated region if either 1) light does not strike the powder overlying the catalyst, or 2) the photoactive powder is isolated for electronic (but not ionic) conduction from its underlying catalyst substrate. Such electronic isolation can be accomplished, for example, by placing the photoactive powder above an additional thin porous film of electrically insulating powder. As a result, an EMF will develop betwen the shielded catalyst region (which now acts as a counter electrode) and an adjacent illuminated region where photocarriers can reach the catalytic substrate. The magnitude of the EMF is proportional to the incident light intensity and also to the concentration of chemical species in an adjacent gas phase. In particular, if a single reactant is present in the gas phase, the light intensity can be adjusted so that the magnitude of the EMF provides a measure of the gaseous reactant.

A sensor structure in accordance with an embodiment of this invention is advantageous. First, material and fabrication costs are low because of the use of semiconductor powders. Second, the highly porous thin film nature of the structure makes the device well-suited to gas-phasea sensing. This is because variations in the concentration of the gaseous reactant to be sensed are quickly established within the sensor structure. Third, the structure is readily adapted to more complex devices. For example, powder layers can be deposited in spatially separate regions using photoresist techniques. This allows for the fabrication of sensor arrays to monitor the spatial distribution of a gaseous species or for the use of different powder materials in different regions. In the latter case, the different materials can provide selective sensitivity to different gaseous species.

DETAILED DESCRIPTION OF THE INVENTION

Figure 3:
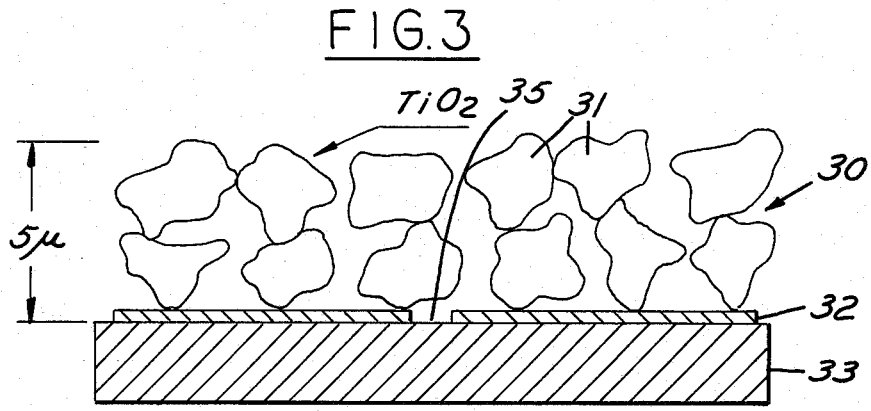
FIG. 3 is a cross section of a powder layer PEC structure having a porous semiconductor layer overlaying a catalytic film supported by a substrate, in accordance with an embodiment of this invention.

Referring to FIG. 3, a powder layer structure 30 has a semiconducting n-type $TiO_2$ powder 31 above a sputtered platinum catalyst film 32 on a substrate 33. To use a specific example, the structure could be used to photosensitize the decomposition of formic acid ($HCOOH \rightarrow H_2 + CO_2$). This reaction is thermodynamically downhill and the structure acts as a photocatalyst.

In a typical sample, $TiO_2$ grains are dispersed in a porous layer with an average thickness ranging from 1–20$\mu$. Advantageously, the porous layer of such semiconductor powder is adapted for photoactivity with a porosity of about 50% to 70%. This layer rests on a sputtered Pt film (approximately 0.1$\mu$ thick) supported by a substrate. A narrow stripe 35 opened in the Pt film permits measurement of the resistivity of the overlying layer of powder 31. The $TiO_2$ is in a powder form with an anatase crystal structure. A typical source of such a powder is Matheson, Coleman and Bell (MCB) with a grain size of approximately 0.2$\mu$ or Degussa P-25 with a grain size of approximately 0.02$\mu$. A grain size less than about 0.2$\mu$ has been found to be advantageous. The grains are made semiconducting (n-type) by reducing them in an $H_2$ atmosphere at 600° C. for several hours. The structure is quickly prepared by dispersing the powder in a polymeric binder sich as methyl methacrylate dissolved in an organic solvent and spinning the solution onto the metallized substrate. The binder is burned off at 250°–300° C., leaving the layer available for further treatment. The detailed morphology of the layer depends on several factors, including degree of dispersion, spin rate ($>$2000 rpm), etc. It is common for the grains (MCB material) to be partially clumped as larger irregular particles with a characteristic dimension on the order of 1$\mu$. Pore dimensions are comparable at about 1$\mu$. The porosity of the layer is estimated at 75%.

The photochemical properites of the structure are investigated by placing a 2 cm$^2$ sample into a 0.20 liter vacuum chamber which is evacuated and then filled with HCOOH at a pressure near its vapor pressure and at an operating temperature of ~25° C. The chamber is equipped with an optical port so that uv photons (supplied, for example, by a 200 watt mercury lamp) illuminate the structure. The optical port includes filters, such as water and colored glass, so that the flux of photons passing through the optical port have an energy above the bandgap energy of the powder (3.1 eV). That is, the filters reduce the light passing through the optical port to photons which are useful in promoting photochemical reactions. A typical photon flux is $2 \times 10^{16}$ sec$^{-1}$. A bellows pump circulates the reactant and product gases in a closed loop. A sampling capillary followed by a cold trap near dry ice temperature passes only $H_2$ and $CO_2$, so that the increase in concentration of $H_2$ and $CO_2$ can be monitored by a mass spectrometer.

To realize high efficiencies, the structure is treated with an electrolyte. For example, aqueous potassium hydroxide can be introduced into the pore volume and then dried to leave small grains of potassium hydroxide in the pore volume. Good results are obtained by dosing the powder layer with approximately 0.2 ml of 10$^2$M NaOH and drying slowly. Subsequently, in the presence of gaseous $H_2O$ and HCOOH, the result is presumably an aqueous solution of HCOONa in the pore volume of the layer. If the volume is completely filled, the electrolyte concentration is on the order of 5 molar. The presence of the electrolyte is detected by resistivity measurements using the open-stripe geometry. Such dosing produces significant ionic conductivity which is correlated with high photochemical activity.

Figure 4:
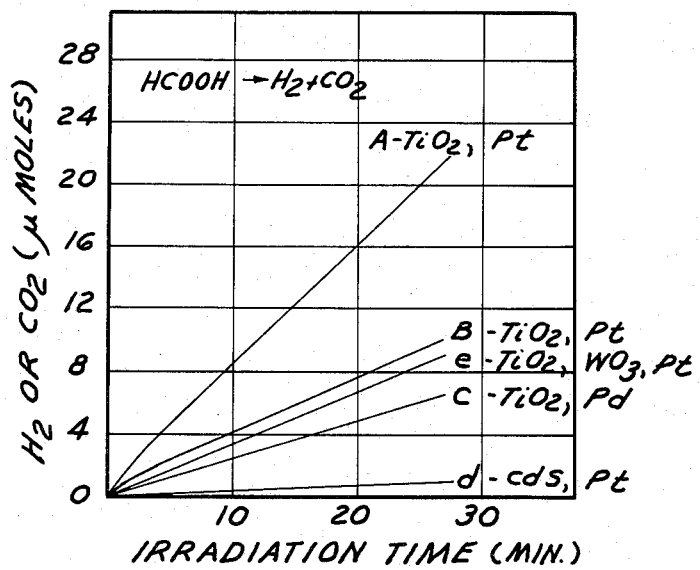
FIG. 4 is a graphical representation of the initial amounts of $H_2$ and $CO_2$ photogenerated versus irradiation time for a number of powder layer parameters when formic acid is used as a reactant: (a) $TiO_2$ ($2\mu$) over Pt; (b) $TiO_2$ ($20\mu$) over Pt, (c) $TiO_2$ ($3\mu$) over Pd, (d) CdS ($5\mu$) over Pt, (e) $TiO_2$ ($3\mu$) over $WO_3$ ($3\mu$) over Pt, in accordance with embodiments of this invention.

FIG. 4 shows the initial rate of $H_2$ growth for a number of different parameters which help illustrate the mechanism of the structure of FIG. 3. In each case, the initial partial pressures are approximately 10 Torr of HCOOH and approximately 20 Torr of $H_2O$. The rate of $CO_2$ growth is nearly identical to that of $H_2$, consistent with the stoichiometry of the reaction. Curve A shows a high rate of growth, corresponding to a quantum efficiency of approximately 40%, for a 2$\mu$ thick film of MCB, $TiO_2$ over Pt. The reaction rate drops by more than a factor of 10$^2$ without the Pt demonstrating its catalytic effect. Curve B shows the effect of increasing the layer thickness to 20$\mu$. Although the rate is reduced it is still significant. Since most of the light is absorbed in the outer 1$\mu$ of the direct gap $TiO_2$, the photocatalytic mechanism must account for the spatial projection of the effect of Pt. Curves C and D show that other materials can be used. Numerous metals including Pd are effective. Some other n-type semiconducting powders including CdS, $Ta_2O_5$ and $SrTiO_3$ are also effective. Semiconducting $WO_3$ over Pt is substantially ineffective. A $TiO_2$ alayer over a $WO_3$ layer (formed by sequentially spinning $WO_3$ and $TiO_2$ layers before binder burnoff) is effective, (see curve E). Finally, no significant photoeffects are observed with below bandgap photons or without a semiconductor powder.

Figure 1:
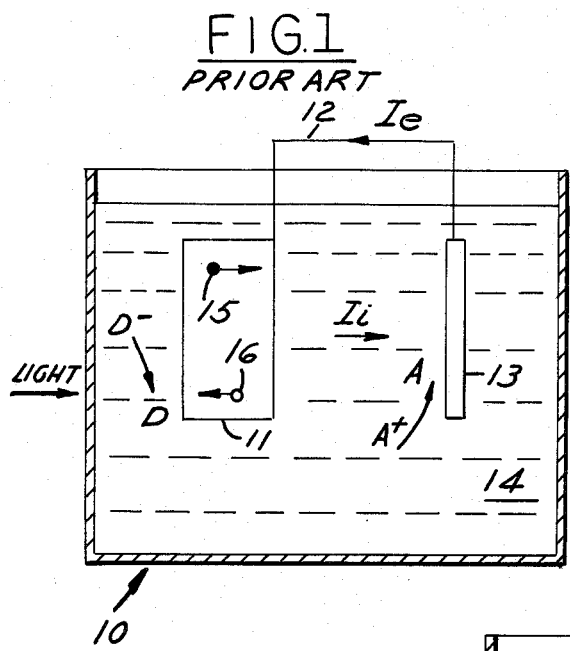
FIG. 1 is a schematic drawing illustrating the operation of a macroscopic PEC cell in which an n-type semiconductor material is illuminated causing redox species $D-$ to be oxidized at a semiconductor surface while species $A+$ is reduced at a counter electrode, in accordance with the prior art.
Figure 2:
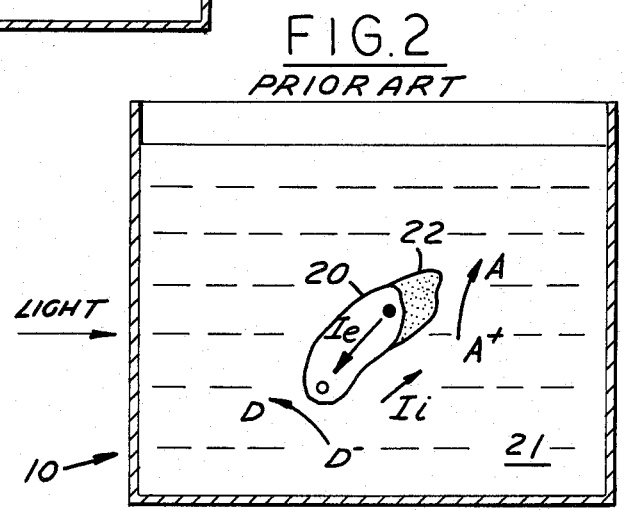
FIG. 2 is a schematic drawing illustrating the operation of microscopic PEC cells having catalyst treated submicron grains of semiconductors immersed in an electrolyte solution, in accordance with the prior art.
Figure 5A:
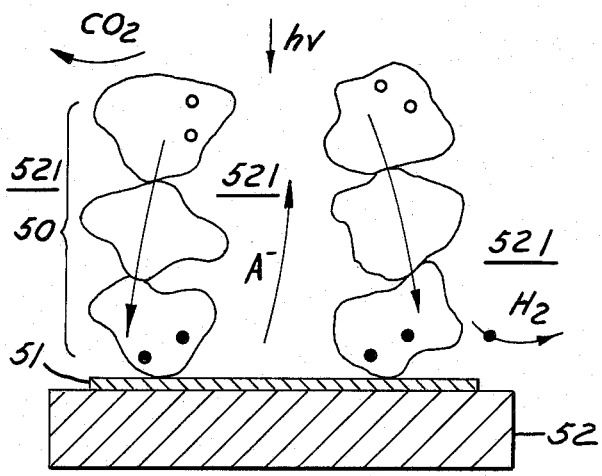
FIGS. 5A and 5B are schematic diagrams for a planar PEC model and an electrical circuit, respectively, in accordance with an embodiment of this invention, for n-type grains in which a coparallel flow of electronic (grains) and ionic (pores) currents results in a spatially dispersed but electrically closed current ($J_P$) loop which supports redox reactions at the upper and lower regions of the porous layer.

FIG. 5A is a planar model of a photocatalytic structure for the photogeneration of complimentary oxidation and reduction products when exposed to light of appropriate wavelengths. This planar model is analogous to the macroscopic and microscopic PEC cells shown in FIGS. 1 and 2, respectively, where similar chemical reactions take place. In FIG. 5A, a porous powder layer 50 over a catalytic film 51 on a substrate 52 acts as a short-circuited photoelectrochemical cell. Photons having above bandgap energy produce electron-hole pairs near the outer region of the powder layer 50. In the presence of an electrolyte 521, surface fields within the n-type grains of layer 50 draw the holes to the outer surface of layer 50 where the holes can oxidize absorbed species (formate ions or formic acid) to form $CO_2$. Electrons migrate to the vicinity of substrate 52 by means of grain contacts. With the catalytic assistance of Pt of film 52, electrons are able to reduce $H_2O$ to $H_2$. the electrical loop is closed by a net migration of ionic species of appropriate sign through the pore volume (or on the outer surface of the grains) of layer 50 in the direction perpendicular to the plane of catalytic film 51.

Figure 5B:
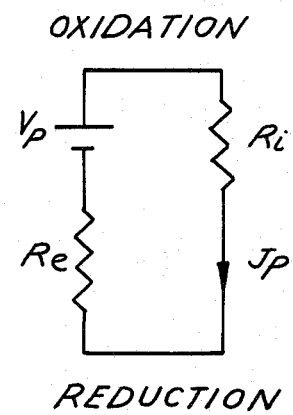

Referring to FIG. 5B, the steady-state electrical model corresponding to FIG. 5A is that of a photovoltage, $V_p$, resulting from the electronic charge separation in series with electronic ($R_e$) and ionic ($R_i$) impedances. Leaving aside the more complex transient photoresponse, the maximum steady-state current flux, $J_p$, corresponding to curve A amounts to approximately 1 mA/cm$^2$. Using the open-stripe geometry, one can estimate a photoinduced electronic resistivity on the order of $10^5$ to $10^4$ ohm-cm with a comparable ionic resistivity. Since conduction path lengths are only a few microns, $V_p$ values on the order of a few tenths of a volt (see below) are adequate to support the current at these resistivity values.

The model of FIG. 5B accounts for the catalytic influence of the Pt, the electrolyte requirement, and accommodates the disparity between layer thickness and optical absorption depth. Corroborating the PEC model of FIG. 5A is the absence of photodecomposition with semiconducting $WO_3$, since its conduction band is positive of the $H_2/H^+$ redox level in aqueous solutions. The fact that photoactivity is strong with a $WO_3$ layer beneath a $TiO_2$ layer demonstrates the importance of electronic conduction through the grains. Photoactivity is greatly reduced when a layer of insulating $Al_2O_3$ is placed below the $TiO_2$ presumably due to the absence of electronic conductivity.

Figure 6A:
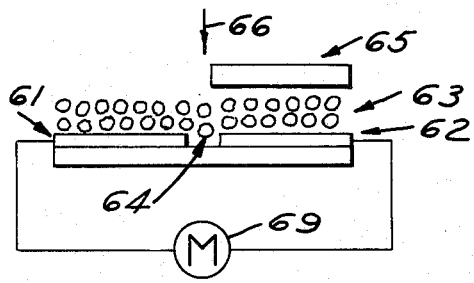
FIG. 6A is a schematic diagram for a powder-layer gas sensor in which the photoactive powder above a region of the thin-film catalyst is obscured from illumination by an opaque light shield so as to permit external circuitry to be attached to the separate regions of the catalyst to monitor the EMF produced by the incident light.

FIG. 6A shows a schematic diagram of a structure adapted to be used as a gas sensor. A powder film 63 is continuous and a conducting catalyst film is split into the catalyst regions 61 and 62, with a nonconducting gap 64 between them. A light shield 65 overlaps catalyst region 62 with one edge of light shield 65 terminating above gap 64 between catalyst regions 61 and 62. Space is allowed between light shield 65 and powder film 63 to allow the ambient atmosphere to be in good contact with a portion of powder film 63 above catalyst region 62. Light 66 is caused to be incident upon the entire structure while in an atmosphere containing water vapor and the gaseous species to be detected. External circuitry 69 coupled between catalyst regions 61 and 62 is available to monitor and record the reduced EMF.

To be specific, consider an example where the ambient contains $O_2$ and $H_2O$ while an n-type $TiO_2$ powder is dosed with a soluble salt to make the pore volume a good electrolytic region. At the illuminated powder surface, photogenerated holes (h+) will cause $H_2O$ to be oxidized according to $2H_2O + 4h+ \rightarrow O_2 + 4H+$. By means of grain contacts, photoelectrons move to the underlying catalyst film where they can reduce gaseous $O_2$ which has penetrated into the pore volume from the ambient by means of the reaction $4e- + O_2 + 4H+ \rightarrow 2H_2O$, where $e-$ represents an electron. The electrical loop is completed by protons flowing in the pore volume from the outer region of the powder layer where they are electrochemically generated to the catalyst layer where they are electrochemically consumed. In the absence of $O_2$, other chemistry will attempted to occur at the catalyst layer. In the ideal case, the electron density will build up on the catalyst until a potential is reached where water (or protons) can be reduced, producing $H_2$ gas. Since this reaction is energetically more difficult to achieve, a large EMF (depending on ligh intensity) will build up between catalyst regions 61 and 62 in the absence of $O_2$. With the presence of $O_2$ in the ambient that EMF will be reduced in an amount proportional to the $O_2$ concentration. Thus, the magnitude of the EMF will provide a measure of the amount of $O_2$ in the ambient. The magnitude of the incident light intensity must be adjusted to accommodate the range of $O_2$ partial pressures and vice versa.

Figure 7:
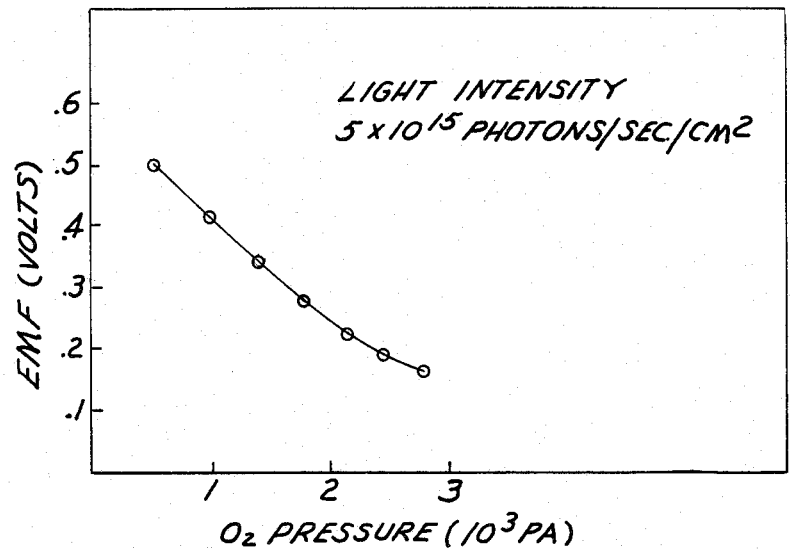
FIG. 7 is a graphical representation of a sensor output EMF for various concentrations of gaseous $O_2$ in a gaseous atmosphere adjacent to a sensor structure of the type shown in FIG. 6B wherein the semiconductor material is reduced $TiO_2$, the catalyst film is Pt, and the light intensity incident on the structure is $5 \times 10^{15}$ photons/cm$^2$-sec with a wavelength above the bandgap of the semiconductor material.

FIG. 7 shows results for an n-type $TiO_2$ (obtained from Degussa Inc.) layer about a Pt substrate. The unshielded region of the sample was illuminated with above band gap light of intensity ($5 \times 10^{15}$ photons/$cm^2$-sec). The data show the EMF (catalyst region 61 more negative than catalyst region 62) generated as a function of $O_2$ concentration in the ambient. The time constant for realizing changes in EMF with changes in gaseous concentration was approximately 20 sec. Similar results were observed when vapor-phase formic and acetic acid were introduced to the ambient atmosphere. Thus, the EMF could be used to sense a number of gases.

Figure 6B:
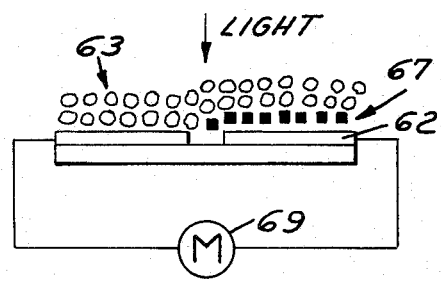
FIG. 6B is a schematic diagram for a powder-layer gas sensor in which the photoactive powder above a region of the thin-film catalyst is isolated for electronic conduction from the catalyst film by a porous, electronically insulating layer of powder such as Al so as to permit external circuitry to be attached to the separate catalyst regions to monitor the EMF produced by the incident light.

FIG. 6B shows another technique for achieving the sensing action without a light shield. The powder region over catalyst region 62 is fabricated using two layers of different electronic conductivities. The outer powder layer 63 is the same photoactive powder used above region 61 while an inner powder layer 67 is made of electronically nonconducting powder such as $Al_2O_3$. Thus, electrons generated in outer powder layer 63 cannot reach the catalyst layer 61 below and an EMF between catalyst regions 61 and 62 can develop. The semiconductor material and catalyst films may be varied to assist designing the best sensor for a given gas.

Alternate electrical detection schemes can be employed to effect the sensing. For example, the two catalyst regions may be connected by a low-impedance current sensitive amplifier. The magnitude of the current flow between the two electrodes decreases with increasing concentration of detectable gas in the ambient and can be used as a sensor of the gas concentration.

Figure 8:
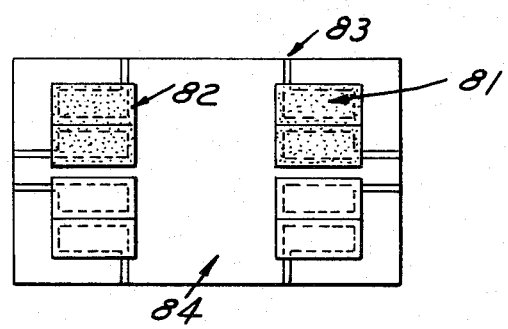
FIG. 8 is a schematic diagram of an array of sensor cells on a single substrate including spatially separated regions of powder and thin-film catalyst prepared suing photoresist techniques.

A useful feature of this approach to gas sensing is the ready ability to fabricate arrays of such cells on a single substrate as shown in FIG. 8. Sensor cells are fabricated on an underlying substrate 84. Catalyst layers 82 and overlying powder layers can be fabricated simply as described below. Regions 83 of metallic catalyst can be used as electrical contact stripes. The fabrication of metallic thin-film patterns for the various catalyst regions is a well established thin-film technology. The same photoresist techniques can also be used to form the required spatially separated powder layer regions. The powder is dispersed in a viscous polymeric photoresist material by stirring or shaking vigorously. The mixture is then spun (e.g. Plat General Spinner) on an appropriate substrate to form a thin film. Using Shipley's 135OJ negative photoresist as an example, UV exposed regions of the mixture can be removed completely with photoresist developer (e.g. Shipley 351 developer) leaving behind a pattern of unexposed mixture. For powder mixtures of useful concentrations for the present work, the presence of the powder in the photoresist does not inhibit the removal of the exposed mixture.

In a final step, the photoresist portion of the remaining pattern can be removed by plasma oxidation (Tegal Corp. Plasmaline 211) leaving only a powder layer pattern suitable for subsequent processing in a thin-film electrochemical device. Arrays of such cells can be used for measuring the spatial dispersion in the concentration of a gaseous species. Alternately, different cells in the array could be fabricated from different materials to allow sensitivity to different gases.

Various modifications and variations will no doubt occur to those skilled in the various arts to which this invention pertains. For example, the geometric configuration of the associated structural components may be varied from that disclosed herein. These and all other variations which basically rely on the teachings through which this disclosure has advanced the state of the art are properly considered within the scope of this invention.

I claim:

1. An electrochemical photocatalytic sensing structure for photosensitizing chemical reduction-oxidation rections so as to sense a gas-phase chemical reactant by electrical means, including:

a nonconducting substrate means for providing physical support for said structure; a film of electronically conducting catalyst material deposited on said substrate means in at least a first and second catalyst regions separated by an open stripe between the regions;

a porous layer of semiconductor power adjacent said catalyst material, and adapted for photoactivity with a porosity of about 50% to 70%, at least some of said semiconductor power being in contact with said catalyst material;

said semiconductor powder including spaced grains of semiconductor material to provide a pore volume to pass a chemical reactant which is subjected to a photochemical reduction-oxidation reaction when said structure is illuminated with light having a wavelength with an energy above the electron bandgap energy of said semiconductor material so that both electron and hole carriers are created in said layer of semiconductor powder;

shield means associated with said first catalyst region to prevent communication of electrons between said semiconductor powder and said first catalyst region; and contact means coupled to each of said first and second catalyst regions to allow measurement of an electrical parameter that develops between said at least two catalyst regions when the powder is illuminated in the presence of a gaseous reactant whose concentration is to be sensed.

2. An electrochemical photocataltyic sensing structure as recited in claim 1 wherein said semiconductor power has a grain size of less than about 0.2 $\mu$m.

3. An electrochemical photocatalytic sensing structure as recited in claim 1 wherein said shield means is an opaque light shield located above said first catalyst region, having an edge substantially aligned with said open stripe between said first and second catalyst regions, and being spaced from said semiconductor power to allow the ambient gas phase to be in communication with the region of said semiconductor powder underlying said opaque light shield.

4. An electrochemical photocatalytic sensing structure as recited in claim 3 wherein the thickness of said semiconductor material layer is in the range of about 1$\mu$ to 20$\mu$.

5. An electrochemical photocatalytic sensing structure as recited in claim 1 wherein said shield means is a porous, electrically nonconducting material positioned between said first catalyst region and said semiconductor powder so as to prevent conduction of electrons between said first catalyst region and said semiconductor powder.

6. An electrochemical photocatalytic sensing structure as recited in claim 5 wherein said porous, electrically nonconducting material includes $Al_2O_3$.

7. An electrochemical photocatalytic sensing structure as recited in claim 1 wherein said contact means is adapted to provide a measurement of an EMF indicating a meaurement of the concentration of the gas phase chemical reactant.

8. An electrochemical photocatalytic sensing structure as recited in claim 1 wherein said contact means is adapted to provide a measurement of a short circuit current whose magnitude provides a measure of the concentration of a reactant gas.

9. An electrochemical photocatalytic sensing structure as recited in claim 1 further including:

an electrolyte material added to said porous layer of semiconductor powder so that said pore volume becomes ionically conducting in the presence of an appropriate chemical reactant.

10. An electrochemical photocatalytic sensing structure as recited in claim 9 wherein:

said grains of semiconductor material are an n-type semiconductor material with a surface adapted to promote an oxidation half reaction of the chemical reactant adjacent said grains of semiconductor material; and said film of catalyst material is adapted to promote a reduction half reaction of the chemical reactant adjacent said catalyst material.

11. An electrochemical photocatalytic sensing structure as recited in claim 10 where said semiconductor powder layer is n-type $TiO_2$, said catalyst material film is platinum, said electrolyte in the pore volume is an alkali hydroxide, and said gaseous reactant is $O_2$ so that upon illumination, the $O_2$ is reduced at the catalyst film and the EMF between the two catalyst regions is reduced from what it would have been without the presence of the $O_2$ thus providing a measure of the oxygen concentration.

12. An electrochemical photocatalytic sensing structure as recited in claim 9 wherein:

said grains of semiconductor material are a p-type semiconductor with a surface adapted to promote a reduction half reaction of the chemical reactant adjacent said grains of semiconductor material; and said film of catalyst material is adapted to promot an oxidation half reaction of the chemical reactant adjacent said catalyst material.

13. An electrochemical photocatalytic sensing structure as recited in claim 1 wherein an array of sensor cells is employed to measure a gaseous concentration over an area.

14. An electrochemical photocatalytic sensing structure as recited in claim 13 wherein said array of cells includes cells of different materials to provide selectivity for sensing different gases.

15. A method of sensing the concentration of a gas by using a photosensitizing chemical reduction-oxidation reaction with an electrochemical photocatalytic sensing structure, including the steps of:

positioning a semiconductor powder in an ambient containing the gas and on two electrical isolated, underlying electronically conducting catalyst layers;

applying light to the semiconductor powder, the light having a wavelength with an energy above the electron bandgap energy of the semiconductor material so that both electron and hole carriers are created in the semiconductor powder; and sensing an electrical parameter between two portions of the semiconductor powder to determine a parameter representative of the concentration of the gas.

16. A method of sensing the concentration of a gas as recited in claim 15 wherein the gas concentration sensed is oxygen concentration and the electrical parameter measured is EMF.

* * * * *